United States Patent [19]
Fabish

[11] 3,949,966
[45] Apr. 13, 1976

[54] VARIABLE CONSTANT FLOW SELECTOR VALVE

[75] Inventor: Donald Clayton Fabish, Anaheim, Calif.

[73] Assignee: Robertshaw Controls Company, Richmond, Va.

[22] Filed: Apr. 30, 1975

[21] Appl. No.: 573,376

[52] U.S. Cl. .............................. 251/206; 251/208
[51] Int. Cl.² ................................................ F16K 3/34
[58] Field of Search .................... 251/208, 207, 206; 137/625.3, 625.31

[56] References Cited
UNITED STATES PATENTS

| | | | |
|---|---|---|---|
| 2,361,655 | 10/1944 | Robinson | 137/625.3 |
| 3,677,516 | 7/1972 | Hicks | 251/208 X |

FOREIGN PATENTS OR APPLICATIONS

| | | | |
|---|---|---|---|
| 450,845 | 8/1949 | Italy | 251/206 |

*Primary Examiner*—Arnold Rosenthal
*Attorney, Agent, or Firm*—Fulwider, Patton, Rieber, Lee & Utecht

[57] ABSTRACT

There is disclosed a fluid flow control valve that provides a plurality of selectable, constant flow rates and that is ideally suited for use with oxygen breathing devices to supply a flow of oxygen to persons in respiratory distress. The valve is simple in construction and designed for minimum size and bulk while insuring accuracy of flow rates. The valve is provided with positive detent indication of the preselected fluid flow rate and can be used in any position on a supporting surface or on the regulator valve of the oxygen supply system. The valve comprises a valve body having a central cavity with a carriage plate received and rotatably supported therein. A first external port communicates with a fluid passageway that extends internally of the body and communicates with a pair of internal ports which are open to the cavity at spaced-apart locations. The carriage plate carries a plurality of orifice members which are of preselected, different orifice sizes and which extend through the carriage plate. The orifice members are positioned at preselected angular orientations relative to the internal ports of the body whereby rotation of the carriage plate moves one of the orifice members into registration with alternate internal ports. The body also has a second external port which is open to the carriage plate thereby establishing fluid communication through said body via an orifice member that is in registration with one of the internal ports of the body. The body also bears a spring-biased detent which is operative to register with one of a plurality of detent receptacles carried on the selector dial of the valve when one of the orifice members is in registration with one of the internal ports. Calibration marks are provided externally of the body with a cooperative index mark carried on the selector dial to provide a visual indication of the preselected flow rate through the valve.

11 Claims, 9 Drawing Figures

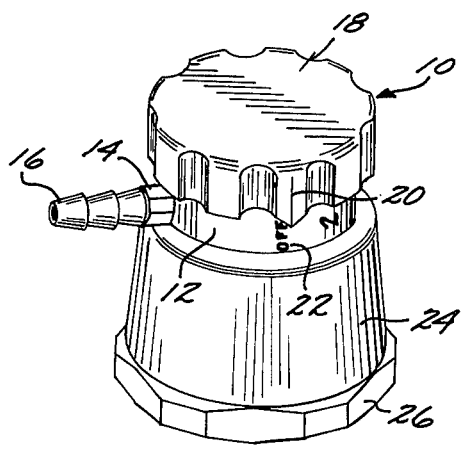
FIG.1
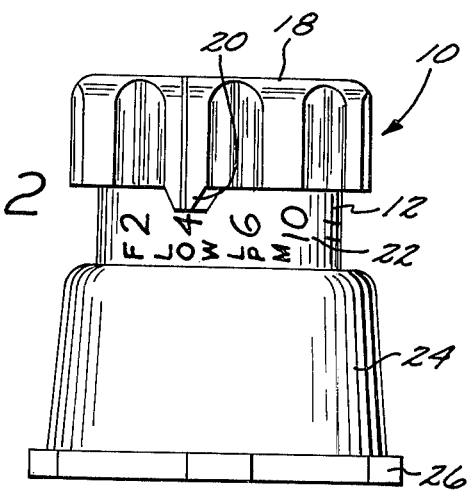
FIG.2
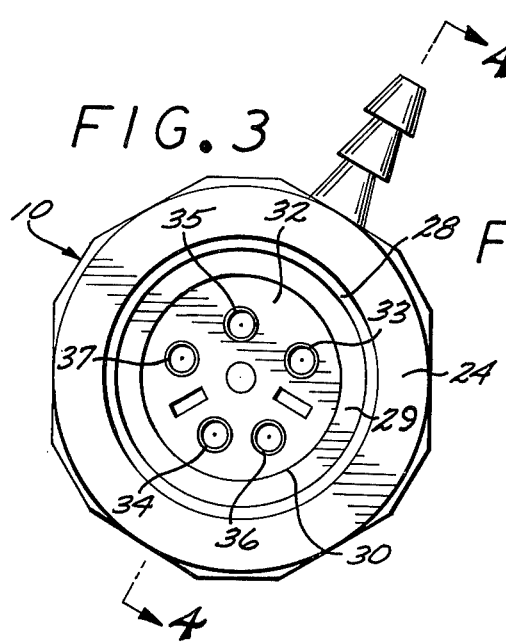
FIG.3
FIG.5
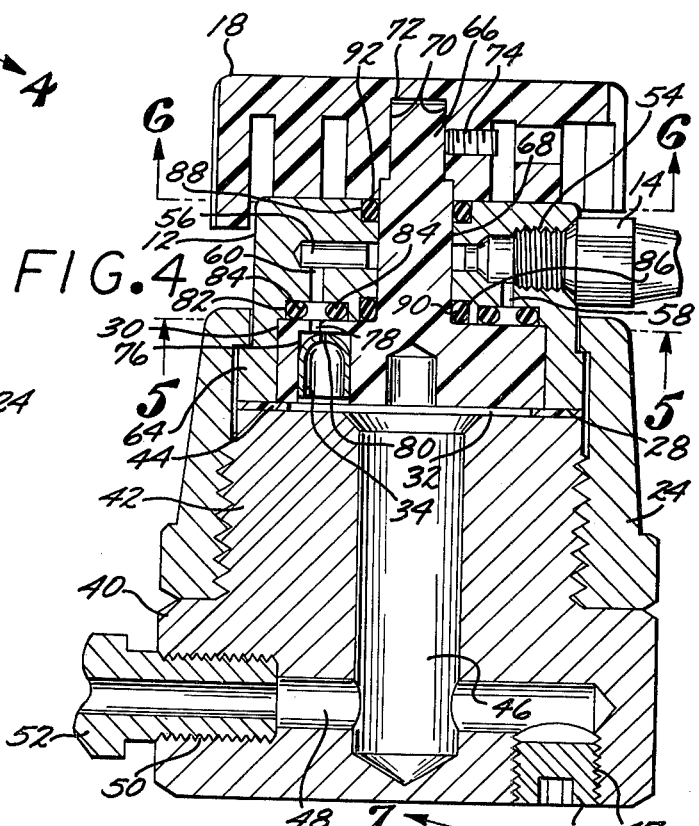
FIG.4
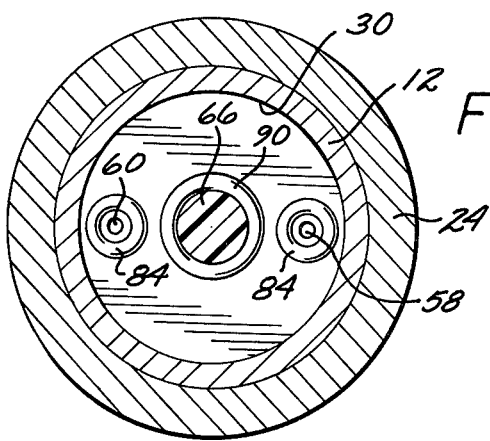
FIG.6
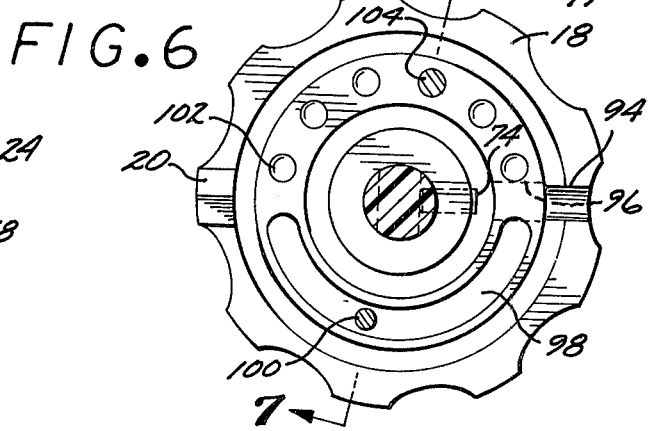

VARIABLE CONSTANT FLOW SELECTOR VALVE

THE BACKGROUND OF THE INVENTION

1. Field of the Invention

This invention relates to a variable, constant flow selector valve, and in particular, relates to a selector valve that is useful in emergency breathing devices.

2. Description of the Prior Art

Emergency respiratory units of the type used in hospitals, ambulances and the like, have typically employed flow control valves in the oxygen line from the pressure regulator of the oxygen cylinder. Commonly, the pressure regulator is set to provide a constant, regulated supply pressure, typically at a set value between about 40 and 90 p.s.i.g. and a manually controlled needle valve and the like is provided to regulate the flow of oxygen to the emergency breathing mask. A flow meter, typically of the rotometer type, is provided in the oxygen supply line to provide a visual indication of the oxygen flow rate to the breathing mask which, typically, is set at a value from 1 to about 15 liters per minute. This equipment is relatively bulky and cumbersome since a rotometer is only operable in a vertical position. The system also demands the complete attention of the operator to adjust the flow rate to a preselected value since the operator must observe the rotometer when setting the flow control valve. Emergency operations in a dimly lit environment can often preclude an accurate setting of the flow rate of the prior devices.

It is, therefore, desirable to provide a variable, constant flow selector valve that is more compact and simple in construction than the previously employed combination of needle valve and rotometer. Additionally, it is desirable to provide a device that can be employed in any position thereby greatly facilitating its use under emergency conditions. It is also desirable to provide such a device with positive detent indication of the preselected constant flow rate, thereby eliminating the need for the visual attention of the operator.

BRIEF STATEMENT OF THE INVENTION

The present invention addresses itself to the aforedescribed difficulties experienced with prior devices. Briefly, the invention comprises a selector valve which provides a plurality of varied, constant flow rates by rotation of one of a plurality of orifice members into registration with one of a plurality of ports carried internally of the selector valve body. The selector valve body has a central cavity that receives a carriage plate rotatably mounted therein and that carries the plurality of orifice members which extend through the carriage plate. The body has an external port open to a fluid passageway extending interiorly of the body into communication with at least two, spaced-apart, internal ports open to the cavity on the received side of the plate member. The opposite side of the plate member is in fluid communication with second external fluid port means. The orifice members are positioned at preselected angular orientations in the carriage plate whereby rotation of the carriage plate sequentially moves an orifice into registration with alternate ports of the plurality of internal ports, thereby establishing fluid communication through the valve body via the one of the orifice members that is in registration with one of the internal ports. The valve body also bears a spring-biased detent that is received in one of a plurality of detent receptacles carried on the undersurface of the selector knob of the valve. Preferably, the body also bears a pin that is received in an arcuate groove on the undersurface of the selector knob to limit the range of rotational movement of the knob, permitting the operator to turn the selector valve to its off position or, by counting the detent stops upon rotation, to preselect any of the variable, constant flow settings.

BRIEF DESCRIPTION OF THE DRAWINGS

The invention will be described with reference to the drawings of which:

FIG. 1 is a perspective view of the selector valve;

FIG. 2 is an elevation view illustrating the flow rate calibration scale of the valve;

FIG. 3 is a view from the inlet port of the selector valve;

FIG. 4 is a sectional elevation view of the selector valve on an adaptor;

FIG. 5 is a view along line 5—5 of FIG. 4;

FIG. 6 is a view along line 6—6 of FIG. 4;

DESCRIPTION OF PREFERRED EMBODIMENTS

Figure 7:
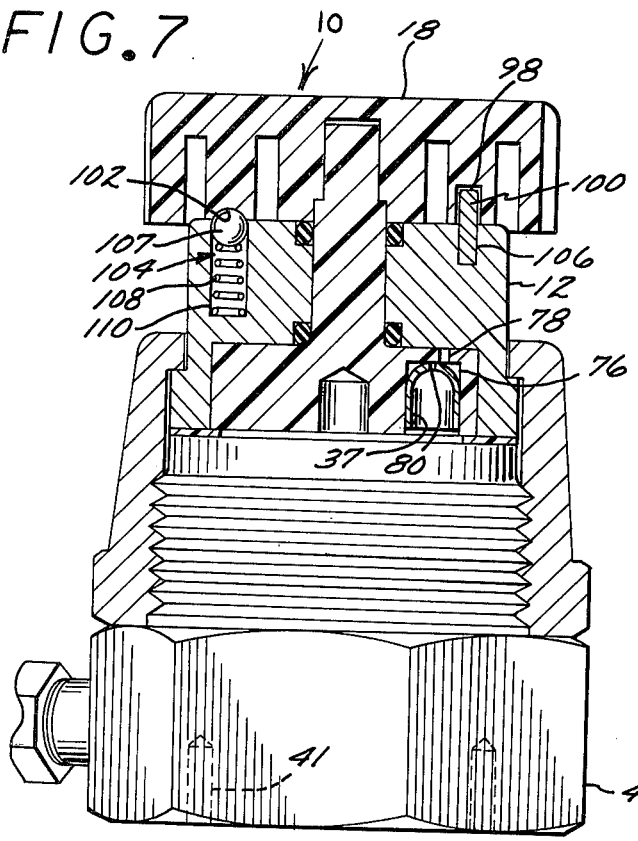
FIG. 7 is a sectional elevation view of the selector valve illustrating the detent means.

Referring now to FIG. 1, there is illustrated the selector valve with selector valve body 12 having an external fluid port that bears hose fitting 14 which is a conventional tubular member having a threaded boss that is seated in the port of the body 12 and that bears a plurality of external, conical skirts 16 for secure engagement to a flexible hose and the like.

The selector valve is provided with a rotatably mounted selector knob 18 which bears an indicator 20 that indexes with indicia 22 on the external wall of body 12, thereby providing a visual indication of the setting of the internal orifice members of the valve mechanism. The lower end of the valve body 12 is received within cap 24 that bears, at its base, wrench flats 26 to permit the threaded attachment of the assembly to standard fittings, adaptors and the like.

Referring now to FIG. 2, the indicia 22 carried externally of body 12 can be seen to comprise a plurality of number designations 2, 4, 6, 10 and 15 which correspond in the preferred embodiment, to gas flow through the device in liters per minute when the device is supplied with a gas at a pressure of from 40 to about 90 p.s.i.g. typical, of the supply pressure of oxygen from the pressure regulator of emergency oxygen facilities.

FIG. 3 illustrates the undersurface of the selector valve 10. Cap 24 bears internal threads 28 for mounting on an adaptor for conventional pipe fittings. Body 12 has a substantially flat undersurface 29 and bears a central cavity 30 in which is rotatably carried carriage plate 32 in which are mounted a plurality of orifice members 33–37.

Referring now to FIG. 4, the valve 10 is illustrated mounted on an adapter base 40 which has a threaded boss 42 that receives the lower, threaded end of cap 24 and that bears against suitable seal means such as washer or gasket 44, to seal against the undersurface 29 of body 12. Adapter 40 bears a central passageway 46 which extends from its inboard surface that is in sealed engagement with gasket 44 and which terminates in fluid communication with a transverse bore 48, the latter being counter-bored at 50 and provided with internal threads to receive a conventional threaded fitting 52. Adapter base 40 is preferably provided with bore 47 which extends from its undersurface into fluid communication with bore 48. Bore 47 bears standard internal threads to receive a gas line fitting such as 52. A plug 49 can be turned into bore 47 to seal this bore when fitting 52 is in bore 48.

Body 12 can be seen to be provided with external port means in the form of internally threaded counter-bore 54 that receives the hose fitting 14 and that is in fluid communication with internal passageway 56 extending transversely through body 12. Passageway 56 is in fluid communication with internal ports 58 and 60 located at spaced-apart positions and in open communication with cavity 30 centrally located in body 12. Received within cavity 30 is carriage plate 32 that is rotatably mounted within cavity 30 on integral shaft 66 that projects through a central bore 68 extending from cavity 30 externally of body 12. The upper end of shaft 66 bears opposed flats 70 which are engaged in a central recess 72 of dial knob 18. A conventional fastening means such as set screw 74 secures the assembly.

Carriage plate 32 bears a plurality of bores 76 in its undersurface which extend a substantial depth and which terminate in small diameter fluid passageways 78 that complete a fluid passageway through plate 64 at each of the bores 76. Each bore 76 receives an orifice member, e.g., 34, which is a generally bell-shaped metal stamping having a convex upper end that is pierced by a small diameter aperture 80 of a predetermined dimension.

Each of the internal ports 58 and 60 is provided with an annular groove 82 that serves as a seat for O-ring seals 84. Annular grooves 86 and 88 are provided about central bore 68 to provide seats for O-ring seal members 90 and 92.

Referring now to FIG. 5, the retainer cap 24 is seen surrounding the lower annular wall of body 12 that encompasses the central cavity 30 within body 12 and that receives the carriage plate 32. The lowermost O-ring seal 90 is seen surrounding shaft 66 and the O-ring seal members 84, which surround the internal ports 58 and 60, appear in the illustration.

Referring now to FIG. 6, there is illustrated the undersurface of the dial knob 18. Dial knob 18 bears indicator 20 on its undersurface. The opposite side of the undersurface of knob 18 is grooved radially at 94 to provide access to set screw 74 that is carried in a threaded bore 96. The undersurface of dial knob 18 also bears an arcuate groove 98 that extends through an arc of approximately 180° and that receives pin 100 that is carried by body 12 and that thereby serves as a stop limiting the range of free rotational movement of dial knob 18 on body 12. The undersurface of dial knob 18 also bears a plurality of detent receiving recesses 102 which are located on a common radius to receive detent means 104 which is also carried on body 12 of the valve.

Referring to FIG. 7, there is illustrated a sectional elevation view along lines 7—7 of FIG. 6. Dial knob 18 is shown with the arcuate groove 98 receiving pin 100 that is carried in a bore 106 in the upper surface of body 12. A detent receiving recess 102 is also illustrated with detent 104 which comprises a spherical bearing 107 biased by compression spring 108 carried within bore 110 in the upper surface of body 12. In the illustrated view, internal ports 58 and 60 do not appear and, accordingly, are not in fluid communication with the illustrated orifice member 37. In this view, the illustrated orifice member 37 is therefore out of fluid communication with the internal passageway through the valve 10.

Adapter base 40 is provided with attachment means for securing it to a supporting surface. The attachment means comprise one or more internally threaded bores 41 which extend into its base and which can receive mounting bolts and the like.

Figure 8:
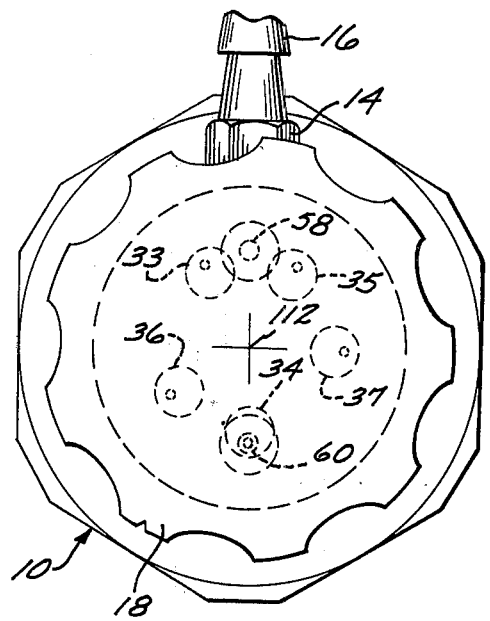
FIG. 8 illustrates the angular relationship of the orifice members to the internal ports of the valve body.

Referring now to FIG. 8, there is illustrated a plan view of the valve 10 showing, in hidden object lines, the angular orientation of the orifice members 33–37. The dial knob 18 is positioned to align orifice member 34 into fluid communication with internal port 60. In this position the opposite internal port 58 is out of alignment with any of the orifice members with orifice members 33 and 35 being disposed to either side of internal port 58. Since each of the orifice members 33–37 is on a separate diameter line of carriage plate 32, i.e., a straight line intersecting the center of rotation 112 and the respective orifice member, it can be seen that only one orifice member, at any time, can be aligned with one of the pair of internal ports 58 and 60.

Each of the orifice members bears a sharp-edged aperture or orifice 80 which is of a distinct and preselected diameter. Upon rotation of the dial knob in a counterclockwise direction, as viewed in FIG. 8, the orifice members are rotated into successive fluid communication with internal ports 58 and 60 in the following order: 33, 34, 35, 36 and 37. The diameters of the sharp-edged orifices 80 in each of the orifice members increase in the afore-indicated order so that these orifices provide the flow rates indicated by the indicia carried externally of the body, i.e., 2, 4, 6, 10 and 15 liters per minute of oxygen when supplied with oxygen at a pressure from 40 to about 90 p.s.i.g.

Figure 9:
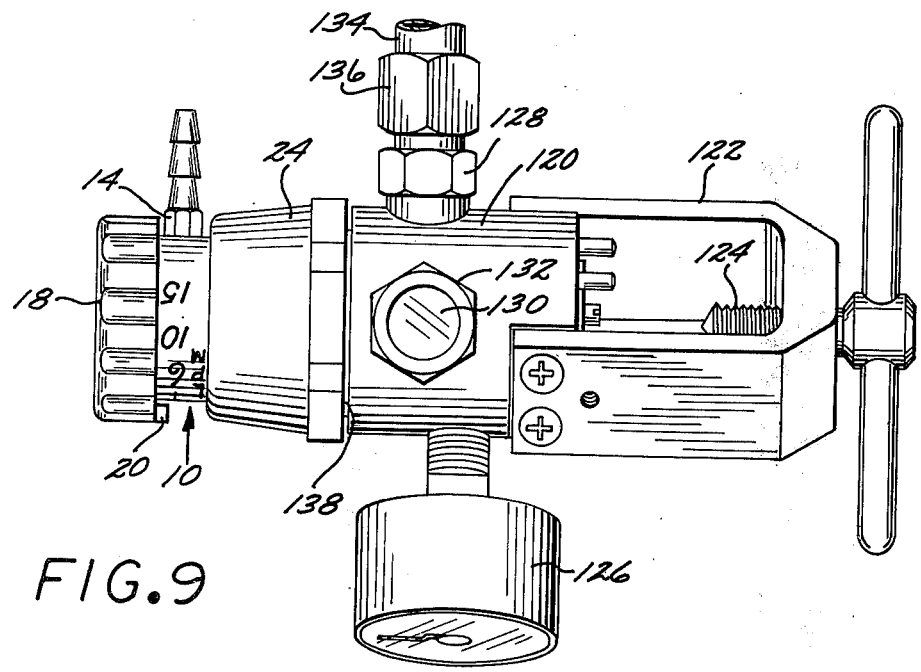
FIG. 9 illustrates the employment of the valve on a typical pressure regulator and oxygen supply system used with emergency respiratory facilities.

Referring now to FIG. 9, there is illustrated a pressure regulator that is conventionally used on an emergency oxygen supply vessel. This regulator comprises a housing 120 that supports yoke member 122 carrying a hand screw 124 for clamping the regulator securely to the supply port of the oxygen cylinder. The regulator housing also supports a cylinder pressure indicator 126 and is provided with two outlet ports which bear conventional pressure fittings such as 128. These ports are supplied with oxygen at a constant pressure by the regulator valve, typically at a pressure from 40 to about 90 p.s.i.g. One of the fittings can be covered by a cap 130 secured by retainer 132 while the other fitting can support a tubular member 134 which is secured by retainer 136 and which extends to other emergency breathing facilities such as the demand valve assembly described in U.S. Pat. No. 3,795,257.

Pressure regulator housing 120 bears a threaded boss 138 on which is fitted cap 24 of the regulator valve 10 of this invention. This assembly thereby provides for a very compact unit of a pressure regulator, which can provide a supply of oxygen pressure at 40 to about 90 p.s.i.g. and a variable, constant flow controller, which can provide a preselected, constant flow of oxygen.

Because dial knob 18 has a rotational detent, the position of the selector valve can be readily determined by an operator without visually observing the position of indicator pointer 20. To make this determination, the operator can turn the dial knob 18 to the limit of its rotational range. When the dial is turned to the limit of its range in a clockwise direction when facing the dial, the selector valve 10 is in its off position. Thereafter, the operator need only count the number of detent positions upon opposite rotation to supply 2, 4, 6, 10 or 15 liters per minute of oxygen to the emergency breathing apparatus.

From the preceding description, it can be seen that the valve of this invention provides a very compact unit which can be employed in any position and can be used for wall or pressure regulator mounting. The detent indexing of the dial knob also provides the operator with a facile indication of the preselected flow rate of the valve without requiring visual observation, thereby greatly facilitating the use of the valve under emergency conditions since it does not distract the operator's visual observation of the patient or present difficulties under dim lighting. The extreme compactness of the valve mechanism is achieved by the plurality of internal ports which are sequentially connected into fluid communication through the valve mechanism by the rotation of the carriage plate 32.

The invention has been described with reference to the presently preferred and illustrated embodiment thereof. It is not intended that the invention be unduly limited by this description of preferred embodiments. Instead, it is intended that the invention be defined by the means and their obvious equivalents set forth in the following claims.

What is claimed is:

1. A variable, constant flow, selector valve that comprises:
    a body having a central cavity open to one end thereof;
    carriage plate means received within said cavity and rotatably carried in said body;
    means carried on said body to effect rotation of said plate within said cavity;
    first external port means carried by said body;
    fluid passageway means extending interiorly of said body from said first external port means;
    at least two internal ports in fluid communication with said fluid passageway means within said body and open to said cavity therein at spaced-apart locations; and
    a plurality of orifice members carried by said carriage plate and extending therethrough to establish fluid communication through said plate means to alternate one of said internal port means, said orifice members bearing orifices of distinct and preselected flow areas whereby the constant flow rate through said valve can be varied by rotation of said carriage plate.

2. The selector valve of claim 1 wherein said plate bears a central shaft, said body bears a central bore receiving said central shaft which extends into engagement with a selector knob external of said body.

3. The selector valve of claim 2 wherein said body bears spring-biased detent means operative to register with one of a plurality of detent receptacle means carried by said dial knob when each of said orifice means is in registration with one of said internal ports.

4. The selector valve of claim 2 wherein said dial knob bears an arcuate groove and said body bears cooperative pin means received within said groove to limit the range of rotational movement of said carriage plate.

5. The selector valve of claim 1 wherein said orifice members comprise cup-shaped members, each having a central orifice, received in bores in the outboard face of said carriage plate means.

6. The selector valve of claim 2 wherein said body bears indicia representative of the gas flow rate through each of said orifice members and said dial knob bears a cooperative index to register the flow rate through said selector valve corresponding to the one of said orifice members that is in fluid communication with one of said internal ports of said body.

7. The selector valve of claim 1 including seal means carried by said body and positioned between said internal ports and the inboard surface of said carriage plate.

8. The selector valve of claim 2 including seal means carried by said body about said central shaft.

9. The selector valve of claim 1 in combination with an adapter comprising a body bearing a threaded neck with a side outlet external port and a retaining ring adapter securing said valve selector body to said neck in sealed engagement to said adapter body.

10. The selector valve of claim 8 wherein said adapter body has a central bore coextensive with said threaded neck and intersecting and in fluid communication with a laterally disposed port.

11. The selector valve of claim 9 wherein said adapter body bears attachment means carried on its undersurface for securing said adapter body to a flat surface.

* * * * *